United States Patent
Beyar et al.

[11] Patent Number: 5,964,771
[45] Date of Patent: Oct. 12, 1999

[54] TEMPORARY STENT SYSTEM

[75] Inventors: Rafael Beyar, Haifa; Oren Globerman, Holon; Mordechay Beyar, Tel Aviv, all of Israel

[73] Assignee: Medtronic InStent Inc., Eden Prairie, Minn.

[21] Appl. No.: 08/472,464

[22] Filed: Jun. 7, 1995

Related U.S. Application Data

[62] Division of application No. 08/040,307, Mar. 30, 1993, abandoned.

[51] Int. Cl.$^6$ .............................. A61F 11/00; A61M 29/00
[52] U.S. Cl. ............................................. 606/108; 606/198
[58] Field of Search ................................... 606/108, 110, 606/113–114, 191, 195, 198

[56] References Cited

U.S. PATENT DOCUMENTS

| | | | |
|---|---|---|---|
| 480,870 | 8/1892 | Harris | 606/113 |
| 3,791,387 | 2/1974 | Itoh | 606/113 |
| 5,108,406 | 4/1992 | Lee | 606/106 |
| 5,122,147 | 6/1992 | Sewell, Jr. | 606/110 |
| 5,336,227 | 8/1994 | Nakao et al. | 606/114 |
| 5,376,094 | 12/1994 | Kline | 606/113 |
| 5,417,684 | 5/1995 | Jackson et al. | 606/113 X |
| 5,417,697 | 5/1995 | Wilk et al. | 606/113 X |
| 5,496,330 | 3/1996 | Bates et al. | 606/113 X |
| 5,562,678 | 10/1996 | Booker | 606/113 |

*Primary Examiner*—Michael Powell Buiz
*Assistant Examiner*—Nancy Connolly Mulcare
*Attorney, Agent, or Firm*—Cowan, Liebowitz & Latman, P.C.; William H. Dippert

[57] ABSTRACT

This application is directed to a stent delivery system for introducing a flexible, generally cylindrical, self-expandable stent. The system comprises a catheter having distal and proximal ends, the catheter defining at least one lumen extending there-through and having at least three longitudinally displaced openings or sets of openings extending from a lumen to the surface of the catheter; a stent which comprises a generally cylindrical, expandable structure having proximal and distal ends and a flexible member extending proximally from the proximal end of the structure, the stent being wound circumferentially around the catheter, and having restraining member holding each of the proximal and distal ends of the stent to the catheter, and one or more restraining member holding at least a portion of the flexible member to the catheter surface; and one or two release wires positioned in and extending longitudinally through at least one lumen, the release wires cooperating with the restraining member so that as the release wire or wires are withdrawn proximally, the proximal and distal end sections of the stent are released in such a manner that coils of the stent unwind.

1 Claim, 3 Drawing Sheets

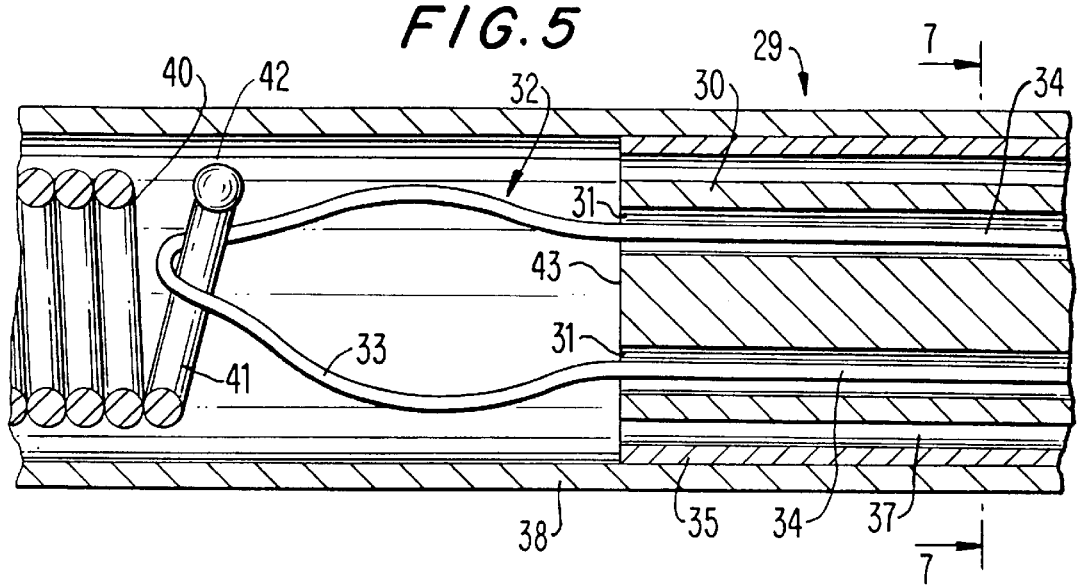
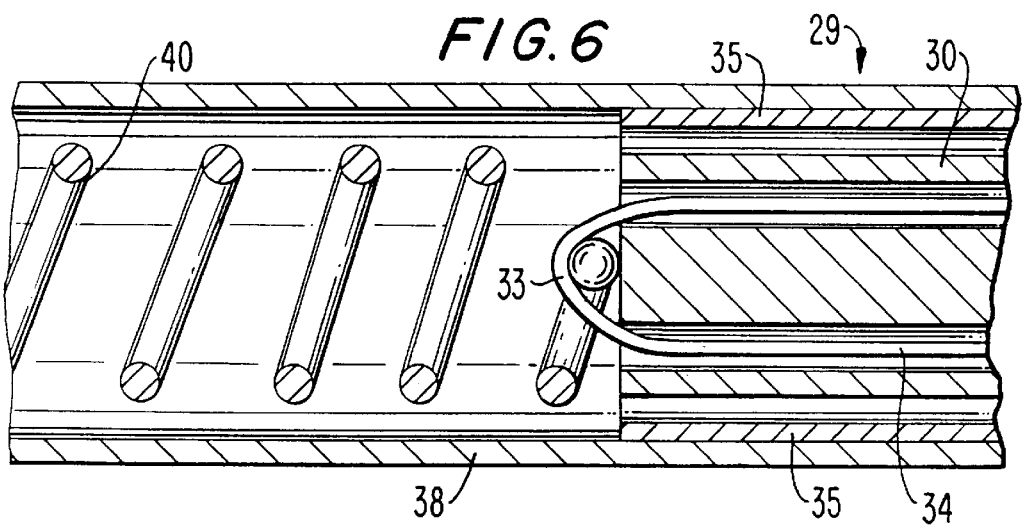
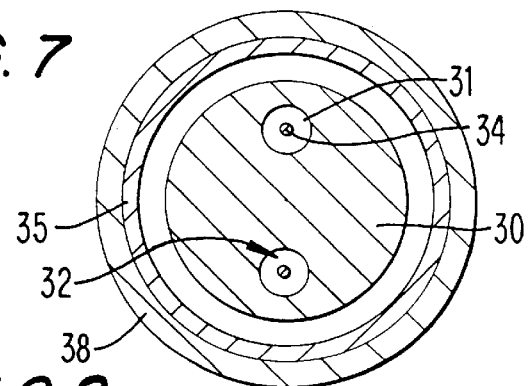
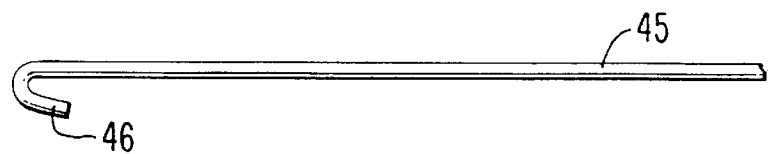

TEMPORARY STENT SYSTEM

This application is a divisional of application Ser. No. 08/040,307, filed Mar. 30, 1993 now abandoned.

FIELD OF THE INVENTION

This invention is directed to devices for the treatment of constricted ducts in human bodies. More particularly, this invention is directed to temporary intravascular, urethral, ureteral, bronchial, oesophageal, and biliary stent systems.

BACKGROUND OF THE INVENTION

Coronary angioplasty has gained wide acceptance as a routine management of coronary stenosis. The technique of the procedure and the manufacture of balloons has improved over the years; however, in spite of such improvements, acute coronary occlusion of a coronary artery, which accounts for about 6% of the cases, continues to be a major concern. Despite improvements in technology and experience, it is still difficult to predict the occurrence of this critical complication.

Accordingly, there is a serious need for treatment for acute occlusions. Several treatment modalities, such as long balloon inflations with the use of a perfusion balloon, laser balloon angioplasty, and, more recently, a temporary stent, have been suggested. However, when such measures fail or become less effective, the patient may require emergency coronary bypass surgery, with which an increased rate of morbidity and mortality is associated.

Temporary stents have been suggested as a method to apply radial force on the occluded segment, thus facilitating free blood flow through the artery to the muscle and tissue at that time. If prolonged radial force is applied, perhaps for up to a few hours or days, then vessel closure may reverse. Possible mechanisms of such reversal are that a dissection flap is tacked to the vessel wall, or that elastic recoil occurs, such as during the first few hours after PTCA is performed.

Despite the theoretical advantage of a temporary stent, there are problems in providing a stent that is readily removable and at the same time easy to insert, flexible, and safe. Most of the known stents intended for coronary and peripheral artery use are not readily removable and require arduous removal techniques or surgical intervention.

SUMMARY OF THE INVENTION

The present invention relates to a device intended for use in dealing with constrictions in ducts of the human body to relieve the possible pathological results of such stenoses. The invention comprises a stent that is configured to be readily removable upon demand from a constricted duct. The temporary stent is to be used in those instances wherein having the stent in position within the constricted duct for a period of from an hour or more to several days is believed to have a positive clinical effect.

OBJECTS OF THE INVENTION

It is an object of this invention to provide a device for the treatment of constricted ducts in human bodies, such as arteries, urethras, ureters, biliary tracts, and the like.

It is also an object of this invention to provide a temporary stent capable of readily, non-traumatic removal from the patient.

These and other objects of the invention will become more apparent in the discussion below.

BRIEF DESCRIPTION OF THE DRAWINGS

FIGS. 5 and 6 are each a partial cross-sectional view of a stent removal system according to the invention;

FIG. 7 is a cross-sectional view of the catheter depicted in FIG. 5; and

FIG. 8 is a partial oblique view of another device useful in the stent removal system shown in FIGS. 5 and 6.

DETAILED DESCRIPTION OF THE INVENTION

Figure 1:
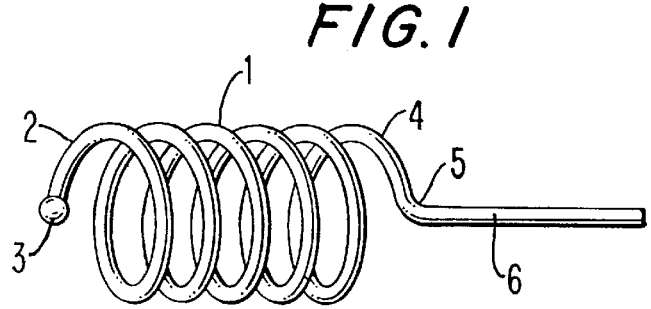
FIG. 1 is a perspective view of a temporary stent comprising an embodiment of the invention.

This invention is directed to a temporary stent and a stent delivery system wherein said stent is releasably held to the distal portion of a catheter. Prior to release the stent is wound over a small diameter catheter where its profile is reduced, and once the stent is released from the catheter, the stent assumes a pre-fabricated diameter by unwinding, reaching a larger diameter profile. The proximal end of the stent continues as a straight, flexible member that extends proximally alongside, i.e., along the outer surface of, the delivery catheter to a point outside the patient's body.

These and other features of the invention may be appreciated better by reference to the drawings. According to FIG. 1, a coiled stent 1 has distal section 2 with ball 3 and proximal section 4 with an angulation area 5. Extending from angulation area 5 is flexible stent wire 6.

Figure 2:
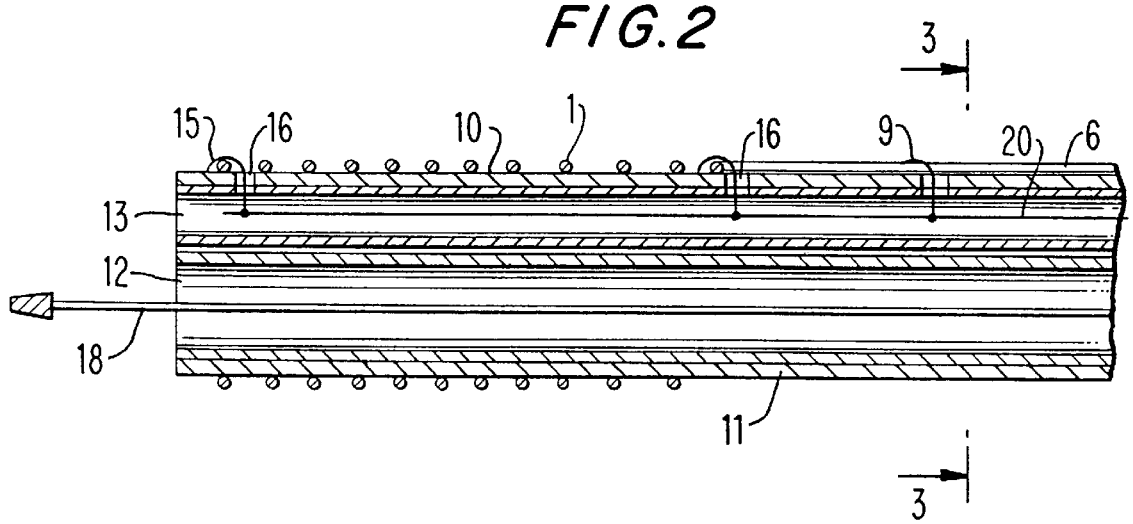
FIG. 2 is a longitudinal, cross-sectional view of a temporary stent delivery system according to the invention wherein a wound stent is positioned on a delivery catheter.
Figure 3:
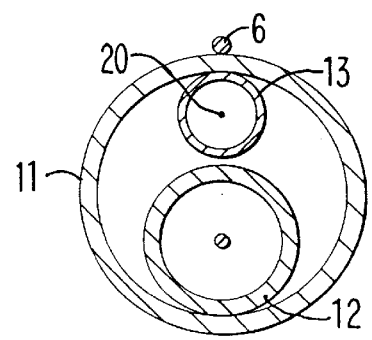
FIG. 3 is a perpendicular, cross-sectional view of a catheter useful in delivering a temporary stent according to the invention.
Figure 4:
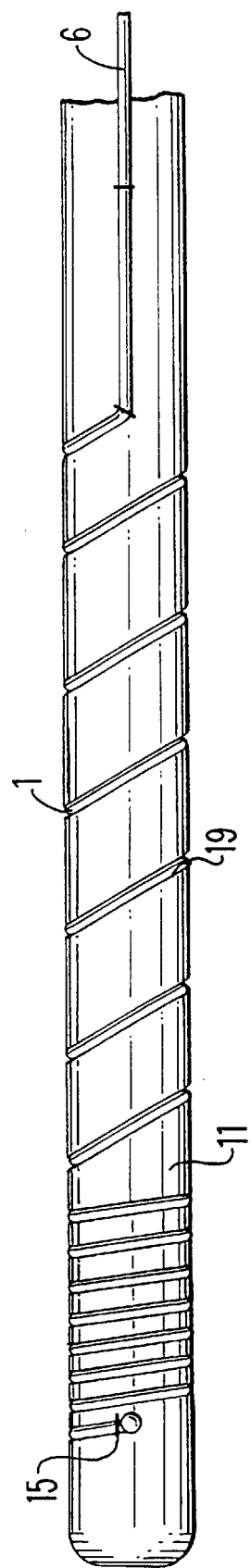
FIG. 4 is a perspective view of a temporary stent delivery system according to the invention.

In FIGS. 2 to 4, the stent delivery system is in its pre-release condition where the coiled stent 1 is affixed to delivery or introducing catheter 11 at the distal and proximal sections 2, 4 of stent 1. The proximal stent wire 6 of the stent is affixed to the catheter surface by a third restraining means 9 to keep the proximal stent wire 6 somewhat coextensive with delivery catheter 11. It is within the scope of the invention that stent 1 when mounted on the delivery catheter can be more tightly wound at distal section 2.

Stent 1 can be releasably affixed to the outer surface 10 of catheter 11 by use of several different methods known in the art. Preferably the affixation consists of loop locking mechanisms 15 that extend over a respective portion, that is, one or more coils, of stent 1 through an opening 16 in the outer surface 10 of catheter 11 to be restrained by one or more restraining means or wires 20 within one or more lumens within catheter 11. Also, restraining means 9, which may be the same as or different from locking mechanism 15, extends over stent wire 6 through an opening 17. Such restraining means or locking mechanisms are discussed in more detail below.

It is also within the scope of the invention that other locking or restraining means could be employed to affix stent 1 to catheter 11. For example, a system such as is shown in U.S. Pat. No. 4,913,141, or in co-pending, commonly assigned U.S. patent applications Ser. No. 07/781,174, filed Dec. 11, 1991, Ser. No. 07/805,737, filed Dec. 10, 1991, Ser. No. 07/827,031, filed Jan. 24, 1992, and Ser. No. 08/009,470, filed Jan. 27, 1993, all of which are incorporated herein by reference, could be employed as well.

Lumen 12 may also serve as a passageway for any other device, such as a guidewire 18, that may be inserted therein. It is within the scope of the invention that catheter 11 may comprise only one lumen or even three or more lumens, as may be required. It is preferable that catheter 11 comprise two lumens, wherein release wire 20 would extend longitudinally within one lumen and a working channel for guidewire or angiography or stent removal would extend longitudinally within another lumen.

As shown in FIG. 2, first distal section 2, next proximal section 4, and then stent wire 6 will be released as release wire 20 is drawn proximally. If there are two or even three separate release wires, one for each of distal section 2, proximal section 4, and/or stent wire 6, respectively, the order of release could be altered or both stent sections, or the stent wire and both stent sections, could be released simultaneously.

In another embodiment of the invention where distal section 2 is more closely wound, stent 1 is sequentially released from catheter 11, as shown in FIGS. 6 to 9 of co-pending, commonly assigned U.S. patent application Ser. No. 08/009,470, filed Jan. 27, 1993, incorporated herein by reference. Preferably the distal section 2 of stent 1 is released and then the proximal section 4 is released. In a stent having a distal closely wound pitch, after release of distal section 2 of stent 1, stent 1 starts to open, i.e., unwind, from the distal end in the proximal direction. Contact of the stent wire with the inner wall of a blood vessel (not shown) would form a groove in the vessel wall with a pitch corresponding to that of the loosely wound stent. However, because the rotating stent increases in diameter, its length decreases slightly in the direction of the proximal portion of the stent, and the tight winding of the end of the stent disappears. The middle section of the released stent 1 should be positioned in substantially the same place, if not the identical place, as the middle of the unreleased stent, assuming the catheter doesn't move during the stent release. At the very least with this configuration it should be possible to reliably predict where the middle of the released stent will be located.

The unwound, released stent 1 shown in FIG. 1 has a longitudinal length approximately 55 to 110%, preferably from about 60 to 95%, of the length of the wound, pre-release stent shown in FIGS. 2 and 4. This relationship will vary dependent upon many factors, such as the tightness of the coils, the stent material, the body tube diameter prior to the stent deployment, and the stent diameter.

As mentioned above, distal section 2 may be more closely wound, although stent 1 as released expands to uniform winding. For example, if the winding of released stent 1 might consist of 15 coils per inch of length, the compressed winding at distal section 2, especially in a temporary stent, could consist of 20 to 45 coils per inch. It is within the scope of the invention that the tightness, i.e., the distance between the coils, of the coils as well as the length of the closely wound coil sections could be adjusted dependent upon the particular application intended. By the appropriate combination of wound and more tightly wound coils, one skilled in the art should be able to easily achieve situations wherein the intravessel released stent 1 will have substantially the same length as that of the originally unwound fabricated stent before mounting on the catheter.

As shown in FIG. 4, the outer surface 10 may have a groove or grooves 19 corresponding to wound stent 1. The groove or grooves 19 are preferably sufficiently deep that the outer diameter of the wound stent is substantially similar to the outer diameter of catheter 11. This arrangement has the advantage of reducing the profile of the delivery system and keeping the differential tightness of the coil pitches during stent insertion into a corporal lumen.

The stent delivery system of the invention is introduced into a patient's body through an appropriate external opening. When the stent is a coronary stent, a guiding catheter of appropriate length is threaded distally through the opening to the origin of the coronary artery, and then a guidewire is advanced distally through the guiding catheter to a desired location. Then, the delivery system of the invention is advanced distally along the guide wire until the stent is situated at the location where dilation or support is desired. As would be appreciated by those skilled in the art, the respective positions of the tip of the guidewire and the stent would be discernible due to appropriate radiopaque markings or features. When the stent is at its desired location, the stent delivery system and stent wire extends proximally to a point outside the patient's body.

After the release wire or wires are pulled proximally, the stent and stent wire are released from the delivery catheter. Preferably the delivery catheter is then retracted along the guidewire, with care being taken not to interfere with the stent wire, and then the guidewire is withdrawn. Optionally (1) the guide wire is withdrawn before the delivery catheter is withdrawn or (2) the guidewire is left in place until the stent is removed.

To withdraw the stent a guiding catheter is advanced distally along the stent wire to the origin of the coronary artery. Through this catheter an angioplasty guidewire is advanced past the site where the stent is located. Over this guidewire and the stent wire, or over only the stent wire, another small diameter catheter is threaded and advanced to a point adjacent the proximal end of the stent, this catheter preferably having a radiopaque marker at its distal end to facilitate locating the catheter distal tip relative to the proximal portion of the stent. Then the stent wire is pulled proximally while the catheter is held in position so that the stent, by rotating, is advanced to the extraction catheter and the coils become sufficiently straightened into the lumen of the catheter, and at the same time the helical part of the stent uncoils in the artery in its own indentations in the arterial wall. During this process of the uncoiling of the arterial part of the stent and its being pulled as a straight wire in the catheter there is no or only minimal trauma to the vessel wall. This process continues till the stent coils are completely removed through the catheter out of the patient's body. Once the stent is pulled into or through the catheter, the small diameter catheter can be withdrawn. At this point, the delivery catheter and an angioplasty wire are left in place. If balloon dilatation or further stenting is required, these can be easily performed over the wire.

The procedure of stent removal could be done without a guiding catheter, by use of a small lumen catheter which is threaded only over the stent wire, or over a stent wire and a guidewire. When the catheter reaches the same position as before, the stent will uncoil as it is pulled as a straight wire into the catheter as described above. However, at the end of the procedure only the small lumen catheter, with or without a guidewire, will be in the coronary artery. Another possibility is threading the small lumen catheter over the stent wire first to the stent location, threading an angioplasty wire through the catheter, advancing the wire distal to the stent, and removing the stent as described before. The advantage of using the guidewire is the safety of stent removal having an angioplasty wire across the lesion in the event of coronary vessel closure.

The delivery catheter itself could be comprised of any polymeric material suitable for such catheters. Useful materials include polyethylene, polyurethane, polypropylene, and co-polymers therewith. The catheter may be comprised of material having differing longitudinal flexibility so that the proximal portion of the catheter is stiffer than the distal tip, enabling easy insertion of the catheter into tortuous vessels. Preferably catheter 11 has a decreased diameter in the area where stent 1 is mounted, to enable the delivery system to have a lower profile at that point, comparable to the diameter of the remainder of the catheter 11. Also, catheter 11 preferably has grooves on its outer surface that correspond to the coils of wound stent 1.

Likewise, the release wires useful herein can be comprised of any physiologically acceptable polymer or metal suitable for such purpose. Stainless steel wires are especially useful in this regard. Also, the distal portion of the release wire can be less stiff than its proximal portion to ensure a flexible tip. This can be accomplished by reducing the diameter of the release wire at its distal end or heat-treating this part of the release wire until it becomes completely or partially annealed.

The catheters useful according to the invention must have at least one lumen suitable for release means, which lumen has three or more openings or sets of openings extending to the exterior surface of the catheter to permit interaction with fixation members. At each fixation point there may be 1 or 2 openings, dependent upon the release means employed. The catheter may comprise a single, concentric, longitudinally extending lumen, or it may comprise one or more eccentric, longitudinally extending lumens.

In the cross-sectional view of FIG. 3, catheter 11 comprises main lumen 12 and side lumen 13, which contains release wire 20. Catheter 11 could instead comprise a single lumen 12, which could be eccentric or concentric within catheter 11. Also, the release wire-containing lumen could contain more than one release wire 20, possibly two or even three release wires if desired.

It is within the scope of the invention that the delivery catheter may be of the "monorail" type, where the catheter has a shortened lumen at the distal end of the delivery catheter. The shortened lumen "tracks" the guidewire while the release wire or wires extend through a separate, full length lumen. The shortened lumen would extend from at or near the distal end of the delivery catheter to a point proximal to the proximal end of the mounted stent. The same kind of catheter can be used to remove the temporary stent.

In some embodiments of the invention, especially the biliary stent or the removable or permanent vascular stent, a middle restraining means is advantageous. However, in some applications, when the stent is closely wound even at its maximum, released diameter, the middle restraining means release mechanism does not function well because it can be caught between two closely wound loops. It was found that a novel arrangement employing a bioabsorbable (or biosorbable) wire straining member is quite effective in overcoming this problem of the loops of the stent which press the middle restraining means and may prevent it from "jumping up," that is, away from the catheter surface. According to the embodiment of the invention set forth in FIGS. 19 and 20 of commonly assigned, co-pending U.S. patent application Ser. No. 08/009,470, filed Jan. 27, 1993, incorporated herein by reference, a release wire extends through a side lumen where it intersects a biosorbable restraining member, which cooperates with the release wire to restrain a portion of the stent. The restraining member can be configured in some different ways, mostly that the restraining means is completely disconnected from the delivery catheter after stent recoiling. As shown in FIG. 19 of application Ser. No. 08/009,470, the restraining member encompasses a portion of the stent, so that when the release wire is withdrawn proximally to release the restraining member and the portion of the stent, the restraining member remains with the portion of the stent or, if the loop were at the distal or proximal portion of the stent, the restraining member may disengage from the stent or stay with it. Alternatively, as shown in FIG. 20 of application Ser. No. 08/009,470, the restraining member is configured so that the respective ends of the restraining member are engaged by the release wire. Therefore, when the release wire is pulled proximally, the ends of the restraining member are disengaged from the release wire, such that the stent member is also disengaged and the stent unwinds. The restraining member may then dissociate from the stent.

The restraining members described above comprise nontoxic, physiologically acceptable material that is preferably biosorbable. Therefore, whether the arrangement of FIG. 19 or FIG. 20 is employed, the restraining member will be absorbed by or passed through the body. Suitable materials are well known to those skilled in the art and would include other materials presently useful for other medical applications, including, but not limited to, the materials used in absorbable sutures such as homo- and copolymers of glycolic acid. See, for example, the materials disclosed in Kirk-Othmer, *Encyclopedia of Chemical Technology*, 2d Ed., Vol. 22, pages 433 et seq., incorporated herein by reference. Examples of such materials are DEXON™ PLUS and DEXON™ "S" available from David+Beck, Inc. of Puerto Rico.

The stent delivery systems described herein are intended to be useful for the stents shown as well as other expandable stents. A preferred stent, such as that shown here, is described in detail in co-pending U.S. patent applications Ser. No. 07/781,174, filed Oct. 31, 1991, and Ser. No. 07/827,031, filed Jan. 24, 1992, both of which are incorporated herein by reference.

More specifically, the preferred stent comprises a spatial spiral (helix) wound of wire of a material tolerated by the human body and which, furthermore, is not corroded or otherwise attacked by body fluids. Such a material, also known as a physiologically or medically acceptable material, could be one or more of several materials known for this purpose. Especially useful here are metals such as stainless steel, gold-plated medical grade stainless steel, stainless steel coated with silicone, bicarbon, or polytetrafluoroethylene, such as TEFLON®, tantalum, titanium, superelastic alloy such as nickel-titanium (Ni-Ti) alloys (commercially available as Nitinol or Tinel), a shape memory polymer, such as are described in U.S. Pat. No. 5,163,952, incorporated herein by reference, or bioabsorbable polymer material such as a saccharide or other biocompatible, nontoxic polymer taught by U.S. Pat. No. 5,141,516, incorporated herein by reference. The stent may be coated with an antithrombotic agent, such as, for example, low molecular weight heparin, to prevent thrombosis. The wire typically has a diameter of from about 0.1 to 1.0 mm, preferably from about 0.15 to 0.60 mm. Also, a strip of ellipsoidal, rectangular, rectangular with step, or S-shape wire is suitable for stent production.

The preferred stent useful herein has thickened regions at the distal end and, optionally, the proximal end of the stent. In the text above reference is made to "ball 3"; however, each ball 3 can be spherical or non-spherical, so long as the "ball" functions as described. Optionally the angulation area 5 may comprise a ball 5A (not shown). For example, in the embodiment shown in FIGS. 1 and 2, the ball 3 (or 5A) could merely be a non-spherical thickened area, such as an egg, cone, or tear-drop shape, or a concentric ball or a ball directed towards the stent central segment or a functionally equivalent loop, hole, or hook, or wire curvature that would cooperate with loop 15 to restrain an end of the stent. The ball 3 (or 5A) may be flattened on its outer and/or inner surface to facilitate the stent being in better contact with the outer surface of the catheter, to enable the mounted profile to be narrower.

The proximal section 4 of stent 1 comprises a flexible wire 6 that extends proximally. Flexible wire 6 is preferably formed as part of stent 1 when stent 1 is manufactured. For example, flexible wire 6 could comprise a thin wire of polymer, stainless steel, or Nitinol that is drawn as the stent 1 is formed. Alternatively, flexible wire 6 can be formed separately from stent 1 and then attached to stent 1 by chemical or mechanical means. Chemical means would include bonding, gluing, melting, or soldering. Mechanical means would include attachment means such as a small clamp or snap or locking arrangement, for example, where the end of the stent is threaded through a hole in flexible wire 6 before a ball 5A is formed. Flexible wire 6 must be made from a physiologically compatible material that may be the same as, or may differ from, the material of stent 1. Further, flexible wire 6 must be of cross-sectional shape and diameter such that it is strong enough to remove the stent 1 but sufficiently flexible for insertion into, and removal from, body passages. Further, flexible wire 6 should be at least 50 cm, preferably from 50 to 300 cm in length, dependent upon the application, to extend toward an opening or to outside the patient's body.

The outer diameter and length of the stent will vary according to the intended use. For peripheral or coronary use, the outer diameter of the unwound stent will typically be from about 4 to 40 French (from about 1.7 to 13.3 mm), and the length of the stent can vary from about 0.5 to 15 cm. It is also within the scope of the invention that the stent may comprise two spirals connected by a wire, the spirals and wire preferably being a continuous wire, or welding at respective distal and proximal ends.

A special property of nickel-titanium alloy (Nitinol) can be used for the production of the stent. Nickel-titanium alloy can have superelasticity at temperatures in the neighborhood of body temperature (37° C.). The term "superelasticity" is used to describe the property of certain alloys to return to their original shape upon unloading after substantial deformation. Superelastic alloys can be strained up to eight times more than ordinary spring materials without being plastically deformed. Such superelasticity would enable one to compress the stent to a very small diameter over the delivery catheter without plastic deformation.

Another aspect of the invention concerns the stent removal system set forth in FIGS. 5 to 8. A stent removal system 29 comprises a catheter 30 with at least two lumens 31 which extend lengthwise through catheter 30. A snare 32 consists of distal section 33, which is continuous with proximally extending sections 34. Sections 34 each extend through respective lumens 31 through and proximal to the proximal portion (not shown) of catheter 30.

A stent such as stent 40 is removed by advancing the stent removal system 29 through a vessel 38 to a position proximal to the proximal end of stent 40, preferably through a guiding or second catheter 35 or other appropriate lumen-containing vehicle. There may optionally be a small space or clearance 37 between catheter 30 and guiding catheter 35. The stent removal system 29 is advanced to the extent that the stent removal system as shown in FIG. 5 is in position such that the distal end 33 is slightly distal of the proximal end 41 of stent 40. Then, the stent removal system 29 is torqued, preferably about one-half turn in the direction opposite to the direction of the stent winding, to engage the ball 42 on stent 40. Next, the snare wires 34 are pulled slowly, but firmly, in the proximal direction to cause the ball 42 of stent 40 to pass against the distal section 43 of catheter 30. Preferably the distal section 33 of snare 32 engages ball 42 to hold it adjacent the distal surface of stent 30 as shown in FIG. 6. As guiding catheter 35 is held stable, stent 30 and snare wire 34 are pulled in the proximal direction, whereupon stent 40 is pulled into guiding catheter 35 and straightens as it is pulled proximally.

In an alternative embodiment, the snare may be of different or configuration sufficient to engage the proximal end of stent 40. For example, the snare could be a single wire 45 having at its distal end a hook 46 or similar configuration that would engage ball 42. Then, as the snare is pulled distally, the hook would engage ball 42 and pull stent 40 proximally to remove it through the guiding catheter. In the case of a single wire snare such as that described here, the catheter 30 need only have one lumen for the snare wire, although it may have other lumens for other purposes.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A stent removal system comprising:

a catheter having distal and proximal ends and defining two or more longitudinally extending lumens, wherein each lumen extends from the distal to the proximal end of the catheter, a snare means consisting of a loop member and two longitudinally extending pull wires, each wire connected to said loop member, the loop member being positioned distal to the distal end of the catheter and each pull wire extending proximally through a lumen in the catheter to a point proximal to the proximal end of the catheter each lumen has only one wire extending proximally therethrough.

* * * * *

UNITED STATES PATENT AND TRADEMARK OFFICE
CERTIFICATE OF CORRECTION

PATENT NO.   : 5,964,771
DATED        : October 12, 1999
INVENTOR(S)  : Beyar et al.

It is certified that error appears in the above-identified patent and that said Letters Patent is hereby corrected as shown below:

<u>Title page,</u>
Item [56], References Cited, U.S. PATENT DOCUMENTS, should also include:
-- 5,019,090    5/1991  Pinchuk        606/194 --

Signed and Sealed this

Twenty-ninth Day of June, 2004

JON W. DUDAS
*Acting Director of the United States Patent and Trademark Office*